US007041216B2

(12) United States Patent
Dunkley et al.

(10) Patent No.: US 7,041,216 B2
(45) Date of Patent: May 9, 2006

(54) CHROMATOGRAPHY COLUMN

(75) Inventors: John Graham Dunkley, Gloucestershire (GB); Neil Francis Frazer, Gloucester (GB); Melvyn John Gill, Gloucestershire (GB)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 10/373,293

(22) Filed: Feb. 24, 2003

(65) Prior Publication Data
US 2004/0164012 A1   Aug. 26, 2004

(51) Int. Cl.
*B01D 15/08* (2006.01)
(52) U.S. Cl. .................. 210/198.2; 210/656; 210/241; 96/101
(58) Field of Classification Search ........... 210/635, 210/656, 659, 189, 198.2, 268, 241, 456; 96/101
See application file for complete search history.

(56) References Cited

U.S. PATENT DOCUMENTS

| 3,919,082 A | * | 11/1975 | Falk ........................... 210/658 |
| 4,350,595 A |   | 9/1982  | Gunkel .................... 210/198.2 |
| 4,451,365 A |   | 5/1984  | Sattler et al. ............. 210/198.2 |
| 4,549,584 A | * | 10/1985 | Morin et al. .................... 141/73 |
| 5,512,168 A | * | 4/1996  | Fetner et al. ............. 210/198.2 |
| 5,667,675 A | * | 9/1997  | Hatch et al. ............. 210/198.2 |
| 5,674,455 A |   | 10/1997 | Marchand et al. ........ 210/198.2 |
| 5,755,559 A | * | 5/1998  | Allington et al. .............. 417/53 |
| 5,893,971 A | * | 4/1999  | Shalon et al. ............. 210/198.2 |
| 6,036,855 A | * | 3/2000  | Shalon et al. ............. 210/198.2 |
| 6,123,849 A |   | 9/2000  | Purdom ................... 210/198.2 |
| 6,139,732 A |   | 10/2000 | Pelletier ................... 210/198.2 |

FOREIGN PATENT DOCUMENTS

| EP | 0078435     | 10/1982 | ............. 210/198.2 |
| EP | 0649019     | 10/1993 | ............. 210/198.2 |
| WO | WO 97/32207 | 9/1997  | ............. 210/198.2 |

* cited by examiner

Primary Examiner—Ernest G. Therkorn

(57) ABSTRACT

The present invention relates to a chromatography column that removes the longitudinal load from the column tube altogether and transfers it to a yoke and stanchion arrangement situated around but external to the column tube. By using the yoke/stanchion system, the central adjuster can be used to move the top end into and out of the housing. Thus, when internal pressure is applied to the column, the tube experiences no longitudinal load. Additionally, the yoke and stanchion design allows for complete removal of the end from the tube without cumbersome disassembly. Moreover, the yoke provides a place to retain the end while the tube is being filled, emptied, cleaned or repaired.

15 Claims, 5 Drawing Sheets

CHROMATOGRAPHY COLUMN

The present invention relates to a chromatography column. More particularly, it relates to a chromatography column that utilizes an external structure to support any longitudinal loads imposed on the column.

BACKGROUND OF THE INVENTION

Chromatography columns have been used for years for the separation and/or purification of different materials such as proteins.

These columns are formed of three basic components; a column tube, a bottom fixed end and a top, movable end. See U.S. Pat. No. 4,350,595 and U.S. Pat. No. 6,139,732. The top end moves relative to the tube so as to be capable of removal for introduction and removal of chromatography media in the tube and to be capable of longitudinal travel into the tube to compress the media for use.

This top end however needs to be fixed at some point to the column in order to move relative to the column.

A first means for accomplishing this is to form a tube of high strength materials, including metals such as stainless steel or rigid structural plastics, such as acrylics or polymethylpentenes such as TPX® plastic available from Mitsui Petrochemical Industries Ltd Corporation of Japan. The tube has a flange at the upper end to which a top plate is attached to the column and a flange at the lower end to which a fixed bottom end is attached. The top, movable end is then attached to this top plate and travels relative to it in and out of the tube.

An example of this type of structure is shown in FIG. 1. The tube 2 has a bottom plate 4 fixed in place by bolts 6 attached to a flange 8 of the tube 2. A top plate 10 is fixed to a top flange 12 of the tube 2 by setscrews 13. A movable end 14 is centrally located in the top plate 10 and is capable, by movement of rod 16, of moving into or out of the tube 2.

As the end 14 moves into the tube 2 to compress the media bed 18 for use, longitudinal forces are carried from the end 14 to the rod 16 to the top plate 10 and then to the tube 2 itself.

The other alternative is shown in FIG. 2. It uses a series of rods 20 or screws closely aligned around the outside of the tube 24 to carry the longitudinal forces rather than the wall of the tube itself. This allows one to use less structurally rigid materials, such as glass or plastics, preferably acrylic or styrene, and to also use thinner walled tubes. All of this reduces the weight and cost of the device.

Most of the elements of that tube 24 of FIG. 2 are similar to those of FIG. 1. One has a movable top end plate 22, a bottom plate 26, attached to a fixed bottom end 27, flanges 28, either as part of the tube 24 or in this example as separate pieces to secure the fixed top plate 30 and bottom plate 26 to the tube 22. A rod 32 extends through the plate 30 and is connected to the movable end 22 by a handle 34. A bed of chromatography media 36 is compressed by the movement of the end 22. Also shown in FIG. 2 are a series of guide rods 36, which are used, in larger columns to keep the end 22 horizontal during movement. Plate 30 is normally affixed on flange 33 and attached by numerous mechanical fasteners 31.

Both of these designs have their limitations. The need to use rigid structural materials for the tube in the embodiment of FIG. 1 limits one's choices of materials and often is more expensive. Also, the materials used are not translucent so that one cannot view the interior of the column. Removing the movable end from the column, such as to add or remove media is a cumbersome task requiring the removal of the top plate and bolts in order to do so. Also, once removed, one must find a place to position these pieces (top plate 10, rod 16 and end 14) where they will not be damaged or contaminated.

The embodiment of FIG. 2 provides one with the ability to use translucent materials such as glass or acrylic; however, the rods (which typically number between 8 and 12 per column) obscure one's view. Moreover, it is even more cumbersome to disassemble. One must disconnect all of the mechanical fasteners 31 from the ends of the rods 20 before removing the top plate 30 and end assembly (22, 32, 34). It too suffers from having to find a place to put these pieces where they will not be damages or contaminated. Further, reassembly is difficult, as one needs to align each of the mechanical fasteners 31 into their respective hole in the top plate 30 and flange 33.

What is needed is a simpler and easier mechanism for handling the longitudinal load of a column and which allows one to easily assemble and disassemble the column as needed.

The present invention provides such a device.

SUMMARY OF THE INVENTION

The present invention removes the longitudinal load from the column tube altogether and transfers it to a yoke and stanchion arrangement situated around but external to the column tube. By using the yoke/stanchion system, the central adjuster can be used to move the top end into and out of the housing. Thus, when internal pressure is applied to the column, the tube experiences no longitudinal load. Additionally, the yoke and stanchion design allows for complete removal of the end from the tube without cumbersome disassembly. Moreover, the yoke provides a place to retain the end while the tube is being filled, emptied, cleaned or repaired.

It is an object of the present invention to provide a chromatography column comprising a base plate, a column tube attached to the base plate in a liquid tight arrangement, a movable top plate capable of moving into and out of the tube and a support structure external of the tube and free of support on the tube to support longitudinal loads imposed on the column.

It is another object of the present invention to provide a chromatography column comprising a base plate, column tube, a bottom edge of the tube being attached in a liquid tight sealing arrangement to the base plate, the base plate having diameter greater than that of the tube, two or more stanchions, each having a lower end and an upper end, the lower ends being attached to the base plate external of the tube, a yoke connected to the two or more stanchions such that it spans the width and centerline of the tube, a central adjuster is formed on the yoke over the centerline of the tube, the adjuster being movably connected to a top surface of a column top end plate so that the top end plate may move into and out of the tube interior.

It is a further object of the present invention to provide a chromatography column using an external set of stanchions and a yoke connected to the stanchions to carry any longitudinal load imposed on the tube of the column and to provide a yoke that is capable of pivoting vertically, horizontally or both about the centerline of the column tube so as to provide free and easy access to the column tube's interior.

It is an additional object of the present invention to provide a chromatography column using an external set of stanchions and a yoke connected to the stanchions to carry any longitudinal load imposed on the tube of the column and to provide a column that allows for the removal or repair of the top plate, tube or bottom plate of the column without complete disassembly of the column.

It is another object of the present invention to provide a modular chromatography column having a base plate capable of holding column tubes of varying sizes and heights, using an external set of stanchions connected to the base plate and a yoke connected to the stanchions wherein the stanchions are formed of two or more pieces and are capable of being adjusted in height by the addition or subtraction of one or more pieces of the stanchions.

IN THE DRAWINGS

DETAILED DESCRIPTION OF THE INVENTION

Figure 1:
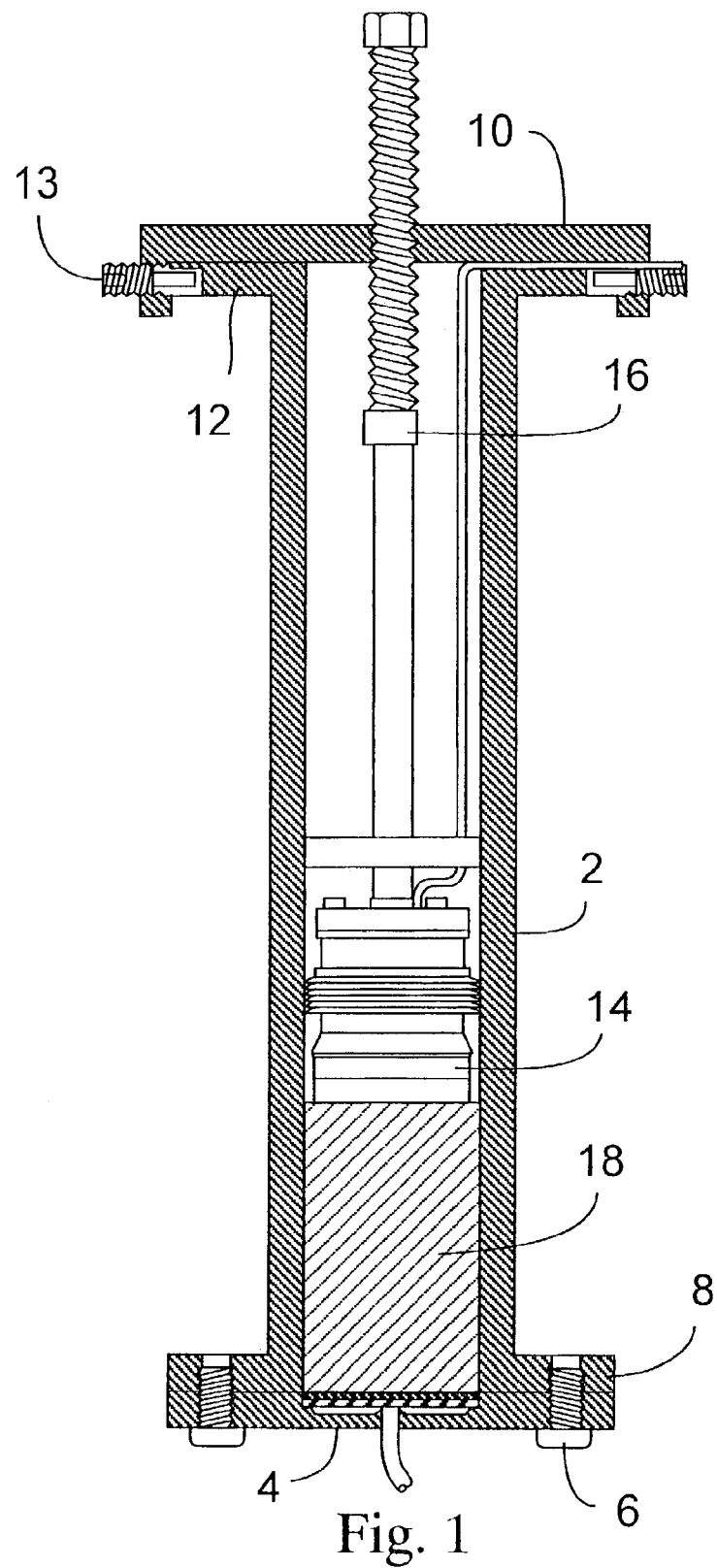
FIG. 1 shows a first embodiment of a prior art column in cross sectional view.
Figure 2:
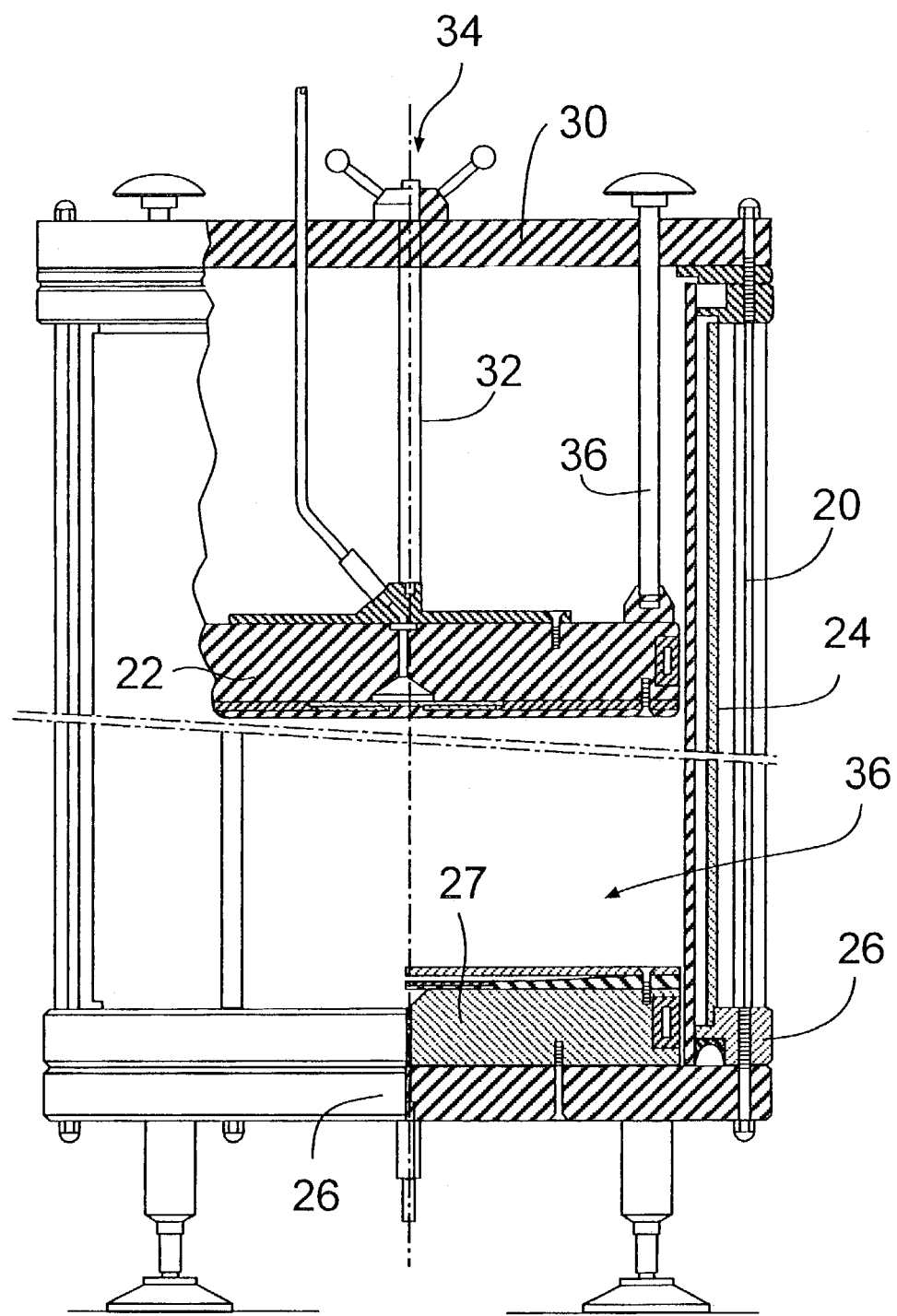
FIG. 2 shows a second embodiment of a prior art column in cross sectional view.
Figure 3:
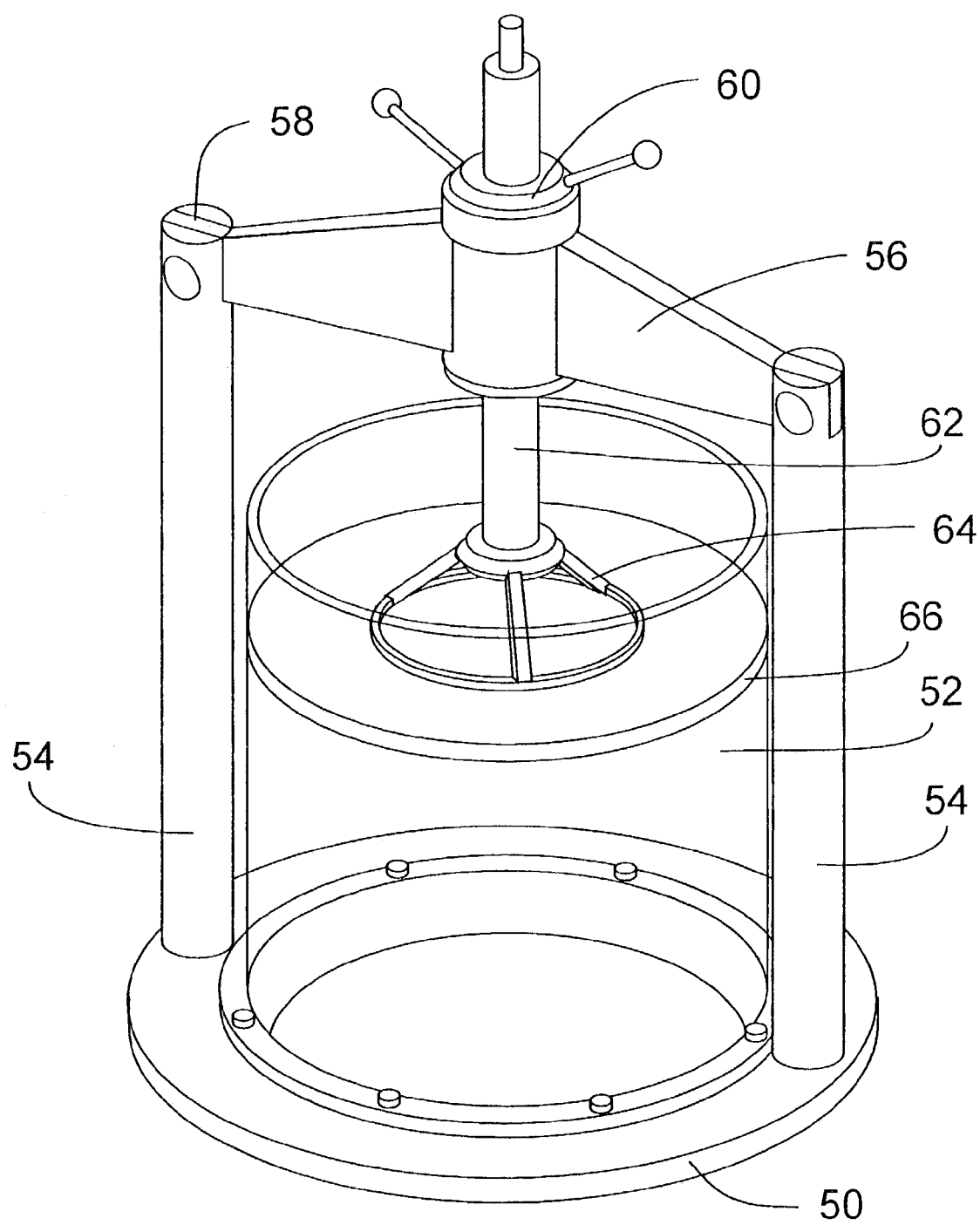
FIG. 3 shows a first embodiment of the present invention in planar view.

FIG. 3 shows a first embodiment of the present invention. The chromatography column consists of a base plate 50 to which the bottom edge of the tube 52 is attached. One can form a flange (not shown) on the bottom edge of the tube, if desired, either as a part of the tube or separately. Unlike in the prior art, as the tube does not bear any longitudinal load, the flange does not need to have significant structural strength, thus one can easily make a flange on an acrylic or glass column.

Alternatives to the flange can be used to secure the bottom of the tube to the base plate 50.

The base plate 50 has diameter greater than that of the tube 52. Arranged around the base plate 50, external to the tube 52 are two or more stanchions 54. The stanchions are structurally strong and typically formed of engineered materials that provide such strength such as metals, including stainless steel and aluminum, composites such as graphite or carbon composites and engineered plastics or composite plastics.

The stanchions 54 have a height equal to or greater than that of the tube 52. Preferably, they have a height that is greater than the tube 52.

A yoke 56 is connected to the two or more stanchions and it spans the width and centerline of the tube 50. The yoke 56 is retained to the stanchions 54 by means such as slot 58 (as shown), a ring or other device that can affirmatively hold the yoke in place. A central adjuster 60 is formed in the yoke 56 over the centerline of the tube 52. The adjuster 60, as shown, uses a screw-threaded rod 62 connected to the top surface 64 of the movable end 66. This central adjuster 60 is used to change the height of the movable end 66 within the tube 52.

Figure 4:
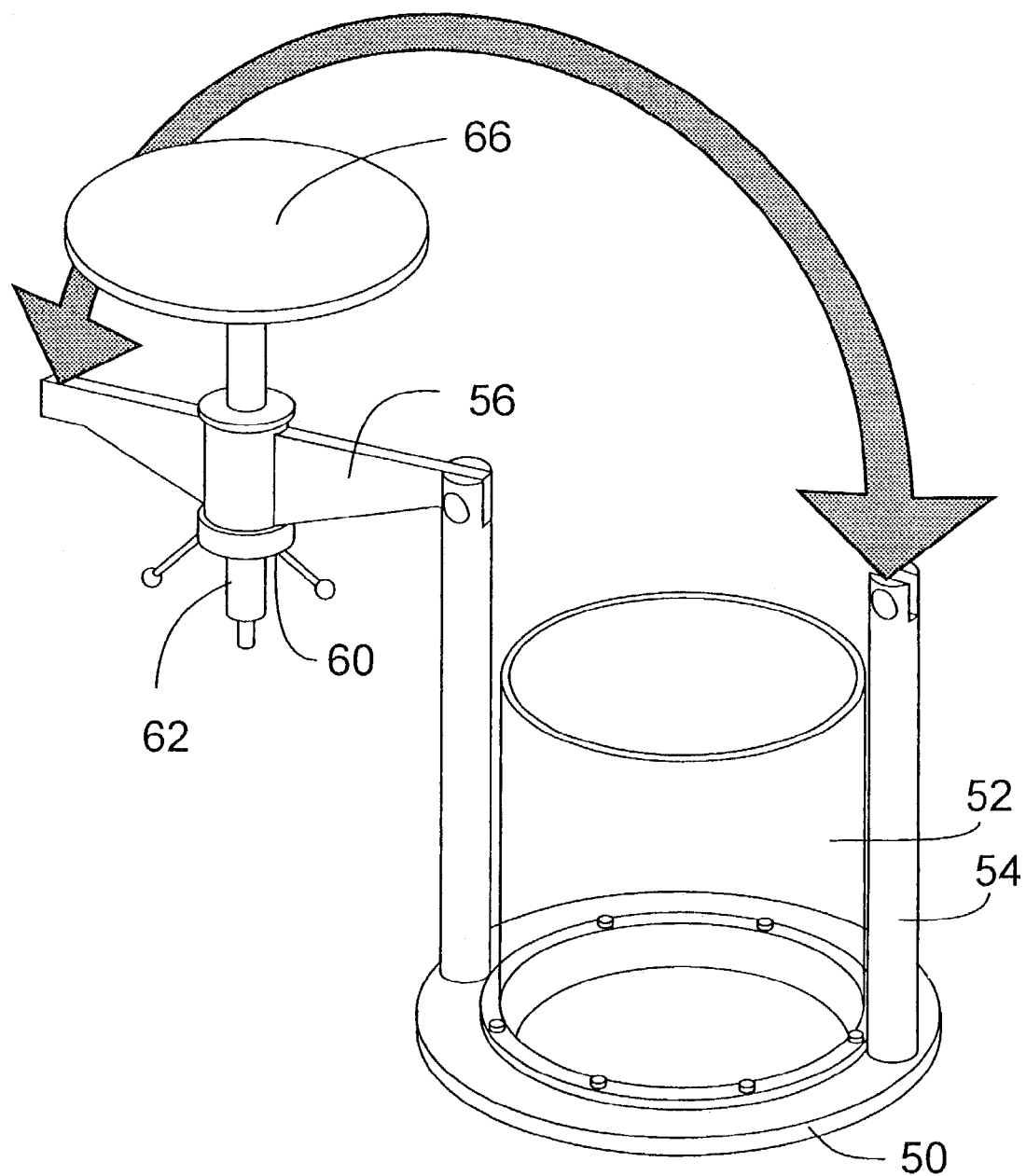
FIG. 4 shows the embodiment of FIG. 3 in a retracted/pivoted position.

The yoke 56 may be permanently attached to the two or more stanchions 54 or if one wishes, it may be removably connected to the stanchions 54 by bolts, clevis pins, cotter pins, clamps and the like. In one preferred embodiment, the yoke 56 is attached to one stanchion 54 by a bolt and the other stanchion by a clevis pin so that when the end 66 is withdrawn from the column by retracting the central adjuster 60 to its uppermost position, the yoke 56 can be pivoted vertically about the stanchion 54 containing the bolt and moved up and out of the way of the tube 50 so as to allow easy access to the column interior. FIG. 4 shows that embodiment in the retracted/pivoted position.

Alternatively, one can form hooks, eyelets or openings (not shown) in or on the yoke 56 such that one may use a crane, come along winch or other such whincing device to vertically lift the yoke 56, central adjuster 60 and end 66 off of the system in order to provide access to the column interior.

In another embodiment, the yoke 56 can also rotate in a horizontal circular motion away from the mouth of the column.

In a further embodiment, the yoke 56 can be detachable from all but one stanchion 54. That stanchion 54 is of a height that the end 66 is out of the tube 52 when the central adjuster 60 is fully retracted. The yoke 56 does not pivot vertically. The stanchion 54 however is capable of horizontal, circular motion away from the tube.

If desired, one may form a stop (not shown) on the yoke 56 or stanchion 54 about which it rotates vertically so as to limit the yoke's 56 range of motion so that it does not pivot to a position where the yoke 56 or end 66 can be damaged.

In a further embodiment, the yoke 56 remains fixed to the one or more stanchions 54. The stanchions 54 have a height that is greater than the height of the tube 52 so that the end may be fully removed from the tube 52 and provide adequate space for one to enter the tube.

The central adjuster 60 may be manually, pneumatically, electrically or hydraulically adjustable between positions or a combination of actuation methods maybe used. Non-manual actuation maybe preferable when additional force, speed or convenience is required.

As the tube wall of the column does not bear any of the longitudinal forces, the materials selected for the tube do not have to be structurally supportive. Glass and various plastics can be used. Suitable plastics are preferably translucent to allow for the viewing of the interior of the column tube. Such plastics include but are not limited to acrylics, styrene, polycarbonate and TPX® polymethylpentene® resin. If desired, metals, such as stainless steel, and other materials typically used in chromatography columns may also be used.

The tube may range in diameter from about 70 mm inner diameter to about 450 mm inner diameter. Its height may also vary from about 500 mm to about 1200 mm.

The base plate may be formed of a metal such as stainless steel, aluminum and the like, a structurally rigid plastic such as TPX plastic or a composite material such as graphite or carbon composite materials.

The diameter of the base plate should be large enough so as to accommodate the column and the stanchions. Preferably, it is circular in shape, to mirror the column, but it need not be so limited. It may be a polygonal shape such as a square, rectangle, pentagon, hexagon, decagon and the like. Alternatively, it may be irregular, providing sufficient area for the column and then having two or more ears extending from it on which the stanchions are mounted.

The stanchions may be formed of any material that provides the necessary strength required. Metals, such as stainless steel, epoxy-coated steel and aluminum are preferred, while engineered plastics such as TPX® plastic or graphite or carbon composites may be used.

Depending upon the load to be supported by the stanchions, they may be solid or hollow. They may also be formed as one piece or if desired several pieces, which are connected together by means such as bolts, clevis pins, mating screw threads and the like. The multiple piece stanchions would allow one to vary the height of the stanchions in relation to the column and would allow one to have a modular column in which different tubes of different heights and/or diameters could be used with a single base and stanchions that are capable of being varied in height.

The stanchions are secured to the base by a variety of means such as welding, bolts, and the like.

Figure 5:
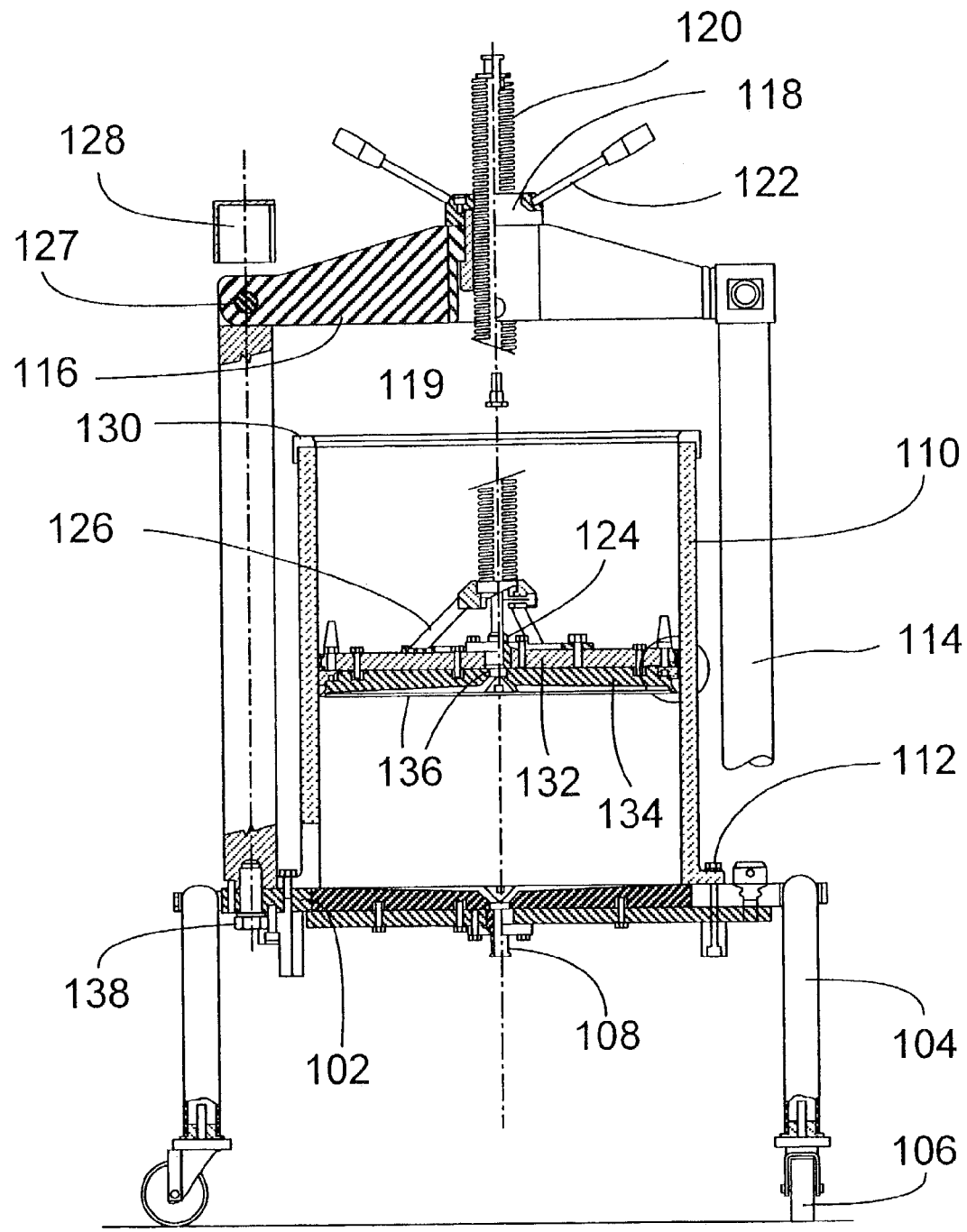
FIG. 5 shows the embodiment of FIG. 3 in cross sectional view.

FIG. 5 shows preferred chromatography system according to the present invention in cross-sectional view, as it would be used in a lab or on a production floor.

The system 100 is comprised of a base 102 that is supported on three or more legs 104. Each leg 104 has a caster wheel 106 on its lower end. The caster wheel 106 may have a lockable brake (not shown) if desired. The base 102 contains a closable opening 108, which forms either an inlet or outlet of the column. In another embodiment, the inlet or outlet on either the central adjuster or base is a more complex valve as disclosed in U.S. Pat. No. 6,123,849. The column tube 110 is mounted on top of the base 102 and secured to it by a series of two or more bolts 112.

Surrounding the tube 100 are two or more stanchions 114. The two or more stanchions 114 are spaced apart from the tube 110 and have a height greater than that of the tube 110. If two stanchions 114 are used, they are diametrically opposite each other. If more than two are used, they are equally spaced about the tube 110. In that embodiment, the yoke 116 will also be formed of several equal arms running from a stanchion 114 to the central adjuster 118. In embodiment of FIG. 5, two stanchions 114 being used, the yoke 116 is a straight single piece, formed of two arms in alignment with each other end meeting at the central adjuster 118.

As shown, the central adjuster has a threaded rod 120 that mates with fixed threads of the adjuster 118. A preferred mechanism is a threaded thrust ring 119 although other means may be used. A rotatable handle 122 is used to move the rod 120 via rotation of its threads against those fixed threads of the adjuster 118.

The lower end of the rod 118 is attached to the movable end plate 124 via a series of equally spaced arms 126 that distribute the force equally around the top of the end plate 124. Alternatively, one could eliminate those arms 126 if they were deemed unnecessary or if other alignment mechanisms were used instead.

The yoke 116 is fixed at each end to the respective stanchions 114 by a locking device 127 such as a nut and bolt, a clevis pin, a spring loaded ball and detent system and the like. As stated above, the yoke 116 may instead be permanently fixed to the stanchions 114, such as by forming the stanchions and yoke of a single piece of material or by welding or adhering the components together. It is preferred however that the yoke 116 be capable of being removed from the stanchions 114 for versatility sake.

A cap 128 may be used over the top of the stanchions 114 after the yoke 114 is in place.

Also as shown in FIG. 5, the yoke 116 has an upwardly tapered profile in cross-section. This is desired but not necessary. The use of a tapered yoke 116 provides additional strength with little material or cost. Alternatively, one could use a linear yoke 116 and make its thickness greater in order to achieve the same result. If desired, the yoke can be forged, machined from a single piece, molded to be a structural beam of regular or irregular shape, formed of a lamination of materials or formed of a series of thinner layers bolted or welded together. A structural beam or laminated beam would be lighter in weight and lower cost and provide all the force transferring properties necessary for the invention.

The top lip of the tube 110 has an optional end plate guide 130 that is used to direct and align the end plate 124 as it moves into and out of the tube 110.

The end plate 124 is typical of that used in a chromatography column and contains a backer plate 132 and a distributor plate 134 and an upper frit or distributor screen 136.

The stanchions 114 are attached to the base 102 and into a threaded recess in the bottom portions of the stanchions 114.

A device as shown in FIG. 5 is operated in the following manner. To load the column, the central adjuster 118 is retracted so that the end plate 124 is out of the tube 110. If desired, the yoke 116 has either been pivoted out of the way or it may be removed altogether as explained above.

The media is placed within the column. If the yoke 116 had been pivoted or removed, it is reattached to the stanchions 114. The end plate 124 is then driven down into the tube 110 past the guide ring 130 by the central adjuster 118. The end plate is adjusted to the desired height, given the type and amount of media used and the desired pressures to be applied.

The chromatography process is run, the captured material eluted and the system is flushed.

To open the column, for example to remove the media, the end plate 124 is retracted from the tube 114 and either left hanging from the yoke 116 above the tube or the yoke is either then pivoted away or removed altogether. The media is then removed either through the top opening of the tube or if desired, through the fixed plate which is arranged with the base plate so as to be removable without the need to disassemble the entire column. This embodiment allows one to simply push the spent media out of the bottom into a catch basin.

The various alternative embodiments presented by the present device are nearly endless. The present invention allows one to use a common base for different sized columns. For example, one could select a series of base plates of varying diameters that allows one to use column tubes of different sizes with basically the same device. For example, the same base plate, yoke and top plate can be used with 70 mm, 100 mm and 140 mm tubes. The stanchions if of sufficient height would not need to be changed. If additional height is required, one can use the multiple piece stanchions discussed above. Alternatively, one can form a single base plate and have an open in its center into which the end plate fits. Various extensions or fixed end plate widths can be formed and used with the same base plate to enable one to use columns of different diameters and heights.

Likewise, as discussed above, stanchions of different heights can be created by using multiple piece stanchions, allowing one to use tubes of different heights with the same equipment.

Also the present invention allows one an easy means for removing or repairing one component of the column without the difficult and time consuming task of disassembling the entire column as was required in the prior art.

As can be appreciated, the present invention provides a chromatography column with several advantages over the prior art.

Through the use of the stanchions and yoke, one eliminates the imposition of longitudinal forces on the column itself. This allows for one to use lighter, less rigid materials for the column tube. It also eliminates the need for many rods attached to the outside of the column, thus making viewing access possible and eliminating the time consuming task of aligning the rods during assembly and removing them during disassembly.

Additionally, by providing a yoke capable of being vertically pivoted and/or horizontally rotated or being capable of removal altogether, one obtains a simple means for retaining the end plate in a position where it is unlikely to be damaged or contaminated during maintenance or repairs.

The system allows for a modular system where columns of different heights or diameters can be used with the same basic equipment.

The system of the present invention allows one to remove or repair of the top plate, tube or bottom plate of the column without complete disassembly of the column.

What is claimed is:

1. A chromatography column comprising a base plate, column tube, a bottom edge of the tube being attached in a liquid tight sealing arrangement to the base plate, the base plate having diameter greater than that of the tube, two stanchions, each having a lower end and an upper end, the lower ends being attached to the base plate external of the tube, a yoke connected to the two stanchions such that it spans the width and centerline of the tube, a central adjuster is formed on the yoke over the centerline of the tube, the adjuster being movably connected to a top surface of a column top end plate so that the top end plate may move into and out of the tube interior and wherein the yoke is selectively attached to the two stanchions such that it may be pivoted away from the centerline of the tube when the top plate has been retracted from the tube.

2. The column of claim 1 wherein the yoke is selectively attached to the two stanchions for removal.

3. The column of claim 1 wherein the yoke is selectively attached to the two stanchions such that it may be pivoted away from the centerline of the tube when the top plate has been retracted from the tube.

4. The column of claim 1 wherein the yoke is selectively attached to the two stanchions such that it may be pivoted away vertically from the centerline of the tube when the top plate has been retracted from the tube.

5. The column of claim 1 wherein the yoke is selectively attached to the two stanchions such that it may be pivoted away horizontally from the centerline of the tube when the top plate has been retracted from the tube.

6. The column of claim 1 wherein the yoke is selectively attached to the two stanchions for removal by a retainer selected from the group consisting of nuts and bolts, clevis pins, cotter pins and clamps.

7. The column of claim 1 wherein the support structure allows one to remove or repair of the top plate, tube or base plate of the column without complete disassembly of the column.

8. The column of claim 1 wherein the two stanchions and the yoke allow one to remove or repair of the top plate, tube or bottom plate of the column without complete disassembly of the column.

9. The column of claim 1 wherein the column tube is interchangeable without complete disassembly of the column.

10. The column of claim 1 wherein the column tube is interchangeable without complete disassembly of the column.

11. The column of claim 1 wherein the column tube, fixed plate and top plate are interchangeable without complete disassembly of the column and by which the column internal diameter size can be altered.

12. A chromatography column comprising a base plate, column tube, a bottom edge of the tube being attached in a liquid tight sealing arrangement to the base plate, the base plate having diameter greater than that of the tube, two stanchions, each having a lower end and an upper end, the lower ends being attached to the base plate external of the tube, a yoke connected to the upper ends of the two stanchions such that it spans the width and centerline of the tube, a central adjuster is formed on the yoke over the centerline of the tube, the adjuster being movably connected to a top surface of a column top end plate so that the top end plate may move into and out of the tube interior and wherein the yoke is selectively attached to the two stanchions such that it may be pivoted away from the centerline of the tube in a direction selected from the group consisting of vertically and horizontally when the top plate has been retracted from the tube.

13. The column of claim 12 wherein the two stanchions are of the same height as the column tube.

14. The column of claim 12 wherein the two stanchions are of a height greater than that of the column tube.

15. The column of claim 12 wherein the upper ends of the two stanchions each have a slot into which the yoke fits.

* * * * *